United States Patent
Petersson et al.

[11] Patent Number: 5,405,373
[45] Date of Patent: Apr. 11, 1995

[54] ELECTRODE DEVICE FOR INTRACORPOREAL TISSUE STIMULATION

[75] Inventors: Mats Petersson, Stockholm; Ulf Lindegren, Enskede, both of Sweden

[73] Assignee: Siemens-Elema AB, Solina, Sweden

[21] Appl. No.: 192,711

[22] Filed: Feb. 7, 1994

[30] Foreign Application Priority Data

Feb. 12, 1993 [SE] Sweden .................. 9300469

[51] Int. Cl.6 ............................................. A61N 1/04
[52] U.S. Cl. .................................. 607/121; 607/116
[58] Field of Search ............ 607/121, 122, 115, 116; 128/642

[56] References Cited

U.S. PATENT DOCUMENTS

| | | |
|---|---|---|
| 3,911,928 | 10/1975 | Lagergren. |
| 4,440,178 | 4/1984 | Bussard et al. ............ 607/121 |
| 4,649,937 | 3/1987 | DeHaan et al. . |
| 4,848,352 | 7/1989 | Pohndorf et al. . |
| 4,995,382 | 9/1990 | Franz et al. . |
| 5,097,843 | 3/1992 | Soukup et al. . |
| 5,181,526 | 1/1993 | Yamasaki et al. ............ 607/121 |

FOREIGN PATENT DOCUMENTS

WO93/00130 1/1993 WIPO.

OTHER PUBLICATIONS

"Decreasing Electrode Size and Increasing Efficiency of Cardiac Stimulation," Furman et al, J. Surg. Res., vol. 11, No. 3, Mar. 1971 (pp. 105–110).

"Plasma Assisted CVD for Biomedical Applications," Grant et al, Diamond and Related Materials, vol. 1 (1992), pp. 727–730.

"Ytforum," No. 6, p. 19 (1992).

Primary Examiner—William E. Kamm
Assistant Examiner—Scott Getzow
Attorney, Agent, or Firm—Hill, Steadman & Simpson

[57] ABSTRACT

An electrode device for intracorporeal tissue stimulation, such as for intracardiac stimulation of heart tissue, includes an electrode cable containing at least one elongated, insulated conductor, and terminating in an electrode head at the distal end of the cable. The electrode head has a surface layer, which defines the shape of the electrode head, formed entirely of electrically conductive material, connected to the conductor, and thereby forming at least one stimulation surface. The surface layer is partially coated with high-resistivity insulating material, the coating forming a layer which is so thin that the difference in the distance between the uncovered portion of the stimulation surface and the heart tissue, and the distance between the insulating coating and the heart tissue, when the electrode device is applied to heart tissue, does not affect the threshold value for tissue stimulation.

3 Claims, 1 Drawing Sheet

ELECTRODE DEVICE FOR INTRACORPOREAL TISSUE STIMULATION

BACKGROUND OF THE INVENTION

1. Field of the Invention

The present invention is directed to an electrode device for intracorporeal stimulation of body tissue, particularly for intracardiac stimulation of heart tissue, of the type having an electrode cable containing at least one elongated, insulated conductor and terminating in an electrode head disposed at the distal end of the cable.

2. Description of the Prior Art

An electrode device of the type generally described above is disclosed in U.S. Pat. No. 3,911,928 wherein the surface of the electrode head partially consists of insulating material and partially consists of electrically conductive material, connected to the conductor, and thereby forming at least one stimulation surface. The head of this known electrode device is provided with a plurality of relatively small conductive surfaces in order to reduce the threshold value, and consequently to reduce energy consumption. This known electrode head has a core of electrically conductive material with preformed parts projecting from the core, with the spaces between these projecting parts being filled with electrically insulating material. The projecting, preformed parts can be strips, a helix, or dots, in order to achieve a strip-like or punctiform distribution of the stimulation area of the electrode head. This known electrode device has the disadvantage that it is complicated, and therefore expensive, to manufacture such an electrode head.

When using an electrode device of the type having an electrode head containing a plurality of small stimulation surfaces, good contact between these surfaces and the heart tissue to be stimulated is essential. In known devices of this type, this means that the insulating material, which constitutes a large part of the surface of the electrode head, must be highly biocompatible so as to reduce the risk of fibrotic tissue being deposited on the electrode head. Fibrotic tissue can grow into a thick layer on the stimulation surfaces, thereby increasing the distance between the stimulation surfaces and the heart tissue to be stimulated, and thereby increasing the stimulation threshold, and thus requiring more power in order to effect stimulation.

SUMMARY OF THE INVENTION

It is an object of the present invention to provide an electrode device of the type having an electrode cable containing at least one elongated insulating conductor and terminating at its distal end in an electrode head having a stimulation surface, which constitutes less than all of the surface of the electrode head, which is simple and inexpensive to manufacture, and which ensures that the stimulation surface, when implanted, achieves good contact with the heart tissue to be stimulated.

It is a further object of the present invention to provide such an electrode device wherein the insulating material, which covers a portion of the surface of the electrode head, is highly biocompatible.

The above objects are achieved in accordance with the principles of the present invention in an electrode device wherein the entire surface layer of the electrode head, which defines the desired shape of the electrode head, consists entirely of electrically conductive material. The electrically conductive material is partially coated with high-resistivity insulating material in a coating layer which is so thin that the difference in distance between the uncovered stimulation surface and the heart tissue, and the distance between the insulating material and the heart tissue, when the electrode device is applied to heart tissue, does not affect the threshold value. By covering the surface of the electrode head with such a thin coating of high-resistivity insulating material, the cost of manufacturing this part of the electrode device can be considerably reduced. In accordance with the invention, the size and shape of the stimulation surfaces can be varied in a simple manner, so as to achieve any desired configuration. The ratio between the size of the stimulation surface and the threshold value in a cardiac electrode device is discussed in an article entitled "Decreasing Electrode Size and Increasing Efficiency of Cardiac Stimulation," Furman et al., Journal of Surgical Research, Volume 11, No. 3, March 1971, pp. 105–110. This article includes a diagram showing that the threshold value drops in relation to the decrease in the size of the stimulation surface. The same article describes and illustrates an electrode head for a ball-head type pacemaker electrode. This ball-head, which serves as a stimulation surface, is so small that it can be regarded as a small-surface electrode. This known electrode, however, has the disadvantage that this size and shape for an electrode head means that the head can easily be damaged and, at worst, may penetrate the heart wall.

Increasing the distance between the stimulation surface and the tissue to be stimulated by 0.1 mm would increase the threshold value by approximately 0.5 V. In this context, it should be noted that the average threshold value for a stimulation surface having an area of 3.5 $mm^2$ is about 0.6 V. The smaller the stimulation surface, the greater the importance of a short distance. In accordance with the invention, therefore, the thickness of the insulating material is preferably in the range of from 0.1 to 10 $\mu m$. A layer of insulation this thin does not, in practice, change the threshold value nor the shape of the electrode head.

In one embodiment of the invention, the insulating material may be extremely hard carbon, i.e., a material known as diamond-like carbon (DLC). This material can be deposited in a very thin layer, but still serves as a high-resistivity insulating material, and it is also highly biocompatible. Since the material is also very hard, the insulating surface of the electrode head is highly abrasion-resistant. The deposition of diamond-like carbon (DLC) films in the context of biomedical instruments is described in the article "Plasma Assisted CVD For Biomedical Applications," Grant et al., Diamond and Related Materials, Vol. 1 (1992), pp. 727–730. The insulating material DLC can be deposited, for example, by means of a laser. An article in the Swedish Trade Journal "Ytform," No. 6, p. 19 (1992), describes the deposition of thin surface coatings in complex patterns by means of a chemical reaction triggered by a fine laser beam, however, there is no discussion therein of the intended use of the surface treated in this manner. This technique, however, is suitable in the context of the present invention. Another technique for manufacturing an electrode head in accordance with the principles of the present invention is to coat the entire surface of the head with a layer of DLC, and then to remove desired areas by means of photo-etching. Thus, a manufacturer, employing a laser or photo-etching, can make a determination as to the manner by which the DLC layer is to be deposited on the electrode surface, and the manner by which the layer is to be worked to achieve the desired pattern.

DESCRIPTION OF THE PREFERRED EMBODIMENTS

Figure 1:
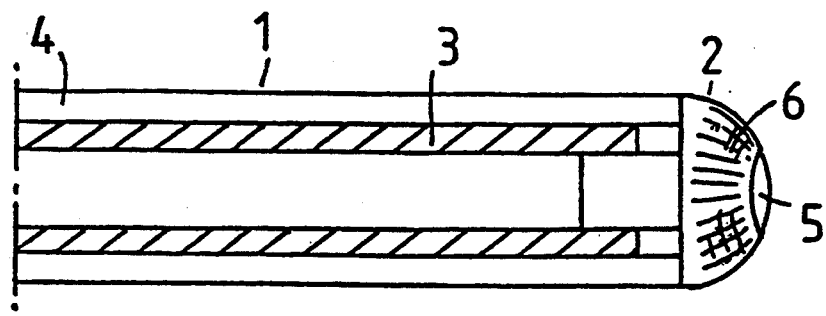
FIGS. 1–3 each show a lateral view of an embodiment of the distal end of an electrode device constructed in accordance with the principles of the present invention, having respectively different patterns of stimulation and insulating surfaces on the electrode head.

FIG. 1 shows the distal end of an electrode device constructed in accordance with the principles of the present invention for intracardiac stimulation of heart tissue in a patient. The electrode device includes an electrode cable 1 having a distal end at which an electrode head 2 is disposed. The electrode head 2 is made of an electrically conductive material, such as titanium nitride, and is connected to an elongated conductor 3 which extends to the proximal end (not shown) of the electrode cable 1 for connection to a stimulation pulse generator. The electrode cable 1 has an external layer of insulation 4. FIG. 1 shows that the electrode head 2 is provided with a round, centrally disposed stimulation surface 5, and the rest of the external surface of the electrode head 2 is coated with a high-resistivity insulating material 6, such as diamond-like carbon (DLC) which is extremely hard and highly biocompatible. This material can be deposited on the surface of the titanium nitride electrode head 2 in a layer or coating which is so thin that the difference in distance between the uncovered stimulation surface and heart tissue, and between the insulating material and the heart tissue, when the electrode device is applied to heart tissue, does not affect the threshold value. In other words, the coating or layer of insulating material 6 does not, in practice, change the shape of the electrode head 2.

Figure 2:
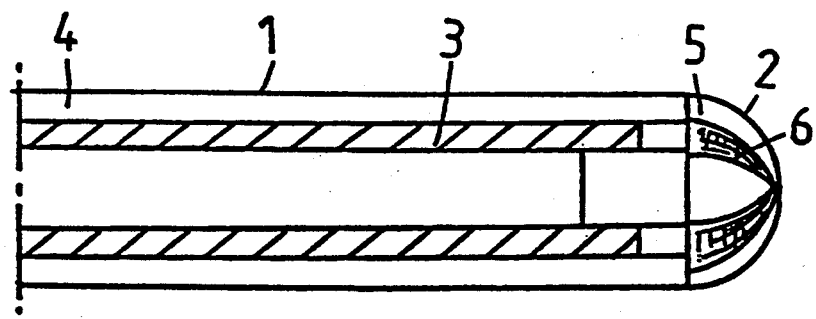

In FIG. 2, the electrode head 2 is shown divided into pie slice-like sections 5 and 6, the sections 5 consisting of uncovered titanium nitride and thus forming a stimulation surface, and the remaining sections 6 being covered by the aforementioned thin layer of insulating material.

Figure 3:
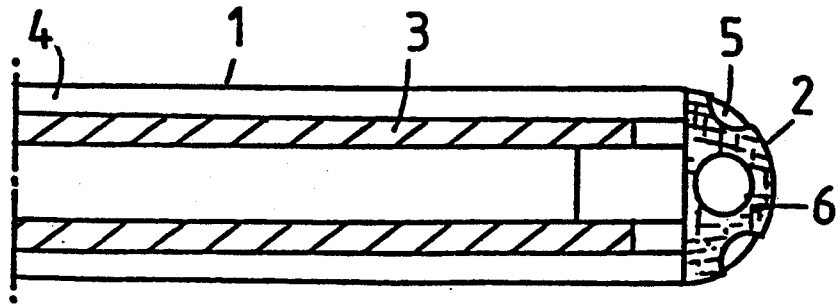

The electrode head 2 shown in FIG. 3 is provided with a number of circular stimulation surfaces, which are insulated from one another by the aforementioned thin coating or layer of insulating material, such as DLC.

The electrode head of the electrode device constructed in accordance with the principles of the present invention is not limited to the illustrated embodiments. The important features of the invention are that the electrode head constructed in accordance with the principles of the present invention is simple and inexpensive to manufacture, and the insulating material with the above-described properties can be readily deposited on the electrode surface of the electrode head in a desired pattern, so as to form a desired number of stimulation surfaces of variable sizes and shapes.

Although modifications and changes may be suggested by those skilled in the art, it is the intention of the inventors to embody within the patent warranted hereon all changes and modifications as reasonably and properly come within the scope of their contribution to the art.

We claim as our invention:

1. In an electrode device for intracorporeal stimulation of body tissue having an electrode cable containing at least one elongated, insulated conductor and terminating in an electrode head disposed at a distal end of the electrode cable, the electrode head being electrically connected to said conductor, said electrode head exhibiting a threshold value and being adapted for application to said body tissue, the improvement comprising:

said electrode head having a surface layer, which defines the shape of said electrode head, formed entirely of an electrically conductive material, and a coating of high-resistivity insulating material partially covering said electrically conductive material so as to provide uncovered regions of conductive material, said coating being so thin that a difference in distance between said uncovered regions and body tissue, and between said insulating material and body tissue, when said electrode head is applied to body tissue, does not affect said threshold value.

2. An electrode device as claimed in claim 1 wherein said insulating material has a thickness in a range from 0.1 to 10 μm.

3. An electrode device as claimed in claim 1 wherein said insulating material consists of diamond-like carbon.

* * * * *